(12) United States Patent
Harbige et al.

(10) Patent No.: US 7,935,729 B2
(45) Date of Patent: May 3, 2011

(54) USE OF TRIGLYCERIDE OILS CONTAINING γ-LINOLENIC ACID RESIDUES AND LINOLEIC ACID RESIDUES FOR THE TREATMENT OF NEURODEGENERATIVE DISEASE

(75) Inventors: Laurence S. Harbige, London (GB); Michael J. Leach, Kent (GB); Mohammed Sharief, Kent (GB)

(73) Assignee: BTG International Limited, London (GB)

( * ) Notice: Subject to any disclaimer, the term of this patent is extended or adjusted under 35 U.S.C. 154(b) by 1013 days.

(21) Appl. No.: 10/555,757

(22) PCT Filed: May 14, 2004

(86) PCT No.: PCT/GB2004/002089
§ 371 (c)(1),
(2), (4) Date: Feb. 22, 2007

(87) PCT Pub. No.: WO2004/100943
PCT Pub. Date: Nov. 25, 2004

(65) Prior Publication Data
US 2008/0090908 A1 Apr. 17, 2008

Related U.S. Application Data

(60) Provisional application No. 60/497,332, filed on Aug. 25, 2003.

(30) Foreign Application Priority Data

May 14, 2003 (GB) .................................. 0311081.4

(51) Int. Cl.
A61K 31/22 (2006.01)
A61K 31/07 (2006.01)
(52) U.S. Cl. ......................................... 514/549; 514/725
(58) Field of Classification Search .................. 514/549, 514/725
See application file for complete search history.

(56) References Cited

U.S. PATENT DOCUMENTS

| | | | |
|---|---|---|---|
| 2,077,371 A | 4/1937 | Relneck et al. |
| 2,617,791 A | 11/1952 | Snelling et al. |
| 3,082,228 A | 3/1963 | Sutherland et al. |
| 3,158,541 A | 11/1964 | Sutherland et al. |
| 3,558,656 A | 1/1971 | Pfieffer et al. |
| 3,658,555 A | 4/1972 | Menz et al. |
| 3,671,557 A | 6/1972 | Pfieffer et al. |
| 3,671,563 A | 6/1972 | Pfieffer et al. |
| 3,676,472 A | 7/1972 | Zilliken et al. |
| 3,748,348 A | 7/1973 | Sreenivasan et al. |
| 3,855,254 A | 12/1974 | Haighton et al. |
| 3,862,972 A | 1/1975 | Heslinga et al. |
| 3,972,907 A | 8/1976 | Baran et al. |
| 3,993,775 A | 11/1976 | Williams |
| 4,048,202 A | 9/1977 | Beek et al. |
| 4,058,594 A | 11/1977 | Williams |
| 4,181,670 A | 1/1980 | Liang et al. |
| 4,607,052 A | 8/1986 | Mendy et al. |
| 4,701,468 A | 10/1987 | Mendy et al. |
| 4,701,469 A | 10/1987 | Mendy et al. |
| 4,826,877 A | 5/1989 | Stewart et al. |
| 4,832,975 A | 5/1989 | Yang |
| 4,851,343 A | 7/1989 | Herbert et al. |
| 4,867,965 A | 9/1989 | Ciaudelli |
| 4,876,107 A | 10/1989 | King et al. |
| 4,938,984 A | 7/1990 | Traitler et al. |
| 5,008,126 A | 4/1991 | Klenmann et al. |
| 5,077,312 A | 12/1991 | Shoyab et al. |
| 5,151,291 A | 9/1992 | Tokairin et al. |
| 5,227,403 A | 7/1993 | Seto et al. |
| 5,306,730 A | 4/1994 | Nagai et al. |
| 5,583,159 A | 12/1996 | Horrobin et al. |
| 5,618,955 A | 4/1997 | Mechoulam et al. |
| 5,658,767 A | 8/1997 | Kyle et al. |
| 5,661,180 A | 8/1997 | DeMichele et al. |
| 5,663,202 A | 9/1997 | Horrobin et al. |
| 5,668,174 A | 9/1997 | Kawagishi et al. |
| 5,674,901 A | 10/1997 | Cook et al. |
| 5,753,702 A | 5/1998 | Bednar et al. |
| 5,776,913 A | 7/1998 | Olgilvie et al. |
| 5,834,512 A | 11/1998 | Akimoto et al. |

(Continued)

FOREIGN PATENT DOCUMENTS

DE 19503993 8/1996

(Continued)

OTHER PUBLICATIONS

Harbige, L.S., et al; "The protective effects of omega-6 fatty acids in experimental autoimmune encephalomyelitis (EAE) in relation to transforming growth factor-beta I (TGF-β1) up-regulation and increased prostaglandin $E_2$ ($PGE_2$) production"; Clin. Exp. Immunol; vol. 122; pp. 445-452 (2000).

Griffiths, Gareth, et al; "$\Delta^{6-}$ and $\Delta^{12-}$desaturase activities and phosphatidic acid formation in microsomal preparations from the developing cotyledons of common borage (Borago officinalis)"; Biochem. J.; vol. 252; pp. 641-647 (1988).

Lawson, L.D., et al; "Triacylglycerol Structure of Plant and Fungal Oils Containing γ-Linolenic Acid"; Lipids, vol. 23, No. 4, pp. 313-317 (1988).

Harbige, L.S., et al; "Prevention of experimental autoimmune encephalomyelitis in Lewis rats by a novel fungal source of γ-linolenic acid"; British Journal of Nutrition, vol. 74, No. 5, pp. 701-715 (1995).

(Continued)

Primary Examiner — Raymond J Henley, III
(74) Attorney, Agent, or Firm — Nixon & Vanderhye

(57) ABSTRACT

Method for treating a patient in need of therapy for a neurodegenerative disease by administering to that patient a therapeutically effective dose of a triglyceride oil containing both γ-linolenic acid and linolenic acid residues as triglyceride ester. The ratio of γ-linolenic acid to linolenic acid residues at the sn-2 position of the triglyceride is at least 0.8. The amount of γ-linolenic acid residues at the sn-2 position is at least 18%. The oil is administered at a dose sufficient to maintain or elevate TGF-β1 levels in the patient at a therapeutic level.

34 Claims, 6 Drawing Sheets

U.S. PATENT DOCUMENTS

| | | | |
|---|---|---|---|
| 5,837,731 A | 11/1998 | Vaddadi |
| 5,869,537 A | 2/1999 | Schreiner et al. |
| 5,914,347 A | 6/1999 | Grinda |
| 5,922,345 A | 7/1999 | Horrobin et al. |
| 5,962,712 A | 10/1999 | DeMichele et al. |
| 5,968,809 A | 10/1999 | Knutzon et al. |
| 5,981,588 A | 11/1999 | Akimoto et al. |
| 5,990,163 A | 11/1999 | Evans et al. |
| 6,015,798 A | 1/2000 | Ogilvie et al. |
| 6,020,376 A | 2/2000 | Pariza et al. |
| 6,051,754 A | 4/2000 | Knutzon et al. |
| 6,080,787 A | 6/2000 | Carlson et al. |
| 6,184,251 B1 | 2/2001 | Stordy et al. |
| 6,201,022 B1 | 3/2001 | Mease et al. |
| 6,214,372 B1 | 4/2001 | Jerome et al. |
| 6,262,119 B1 | 7/2001 | Ferrante et al. |
| 6,306,908 B1 | 10/2001 | Carlson et al. |
| 6,331,568 B1 | 12/2001 | Horrobin et al. |
| 6,340,485 B1 | 1/2002 | Coupland et al. |
| 6,340,705 B1 | 1/2002 | Obukowicz et al. |
| 6,361,806 B1 | 3/2002 | Allen et al. |
| 6,410,078 B1 | 6/2002 | Cain et al. |
| 6,410,288 B1 | 6/2002 | Knutzon et al. |
| 6,426,100 B2 | 7/2002 | Watkins et al. |
| 6,426,367 B1 | 7/2002 | Das |
| 6,479,070 B1 | 11/2002 | Cain et al. |
| 6,479,544 B1 | 11/2002 | Horrobin |
| 6,495,536 B1 | 12/2002 | Masui et al. |
| 6,528,040 B1 | 3/2003 | Pearson et al. |
| 6,537,750 B1 | 3/2003 | Shorrosh |
| 6,555,579 B2 | 4/2003 | Kritchevsky |
| 6,566,543 B2 | 5/2003 | Mechoulam et al. |
| 6,576,252 B2 | 6/2003 | Schwartz et al. |
| 6,624,195 B2 | 9/2003 | Horrobin |
| 6,630,157 B1 | 10/2003 | Horrobin et al. |
| 6,673,840 B1 | 1/2004 | Oh et al. |
| 6,677,470 B2 | 1/2004 | Saebo et al. |
| 6,689,812 B2 | 2/2004 | Peet et al. |
| 6,841,573 B2 | 1/2005 | Llewellyn |
| 6,852,757 B2 | 2/2005 | Jerome et al. |
| 6,858,416 B2 | 2/2005 | Murkerji et al. |
| 6,864,242 B2 | 3/2005 | Ernest |
| 2001/0047036 A1 | 11/2001 | Vanderhoof et al. |
| 2002/0022658 A1 | 2/2002 | Das |
| 2002/0051964 A1 | 5/2002 | Surai et al. |
| 2002/0065319 A1 | 5/2002 | Horrobin |
| 2002/0072539 A1 | 6/2002 | Mechoulam et al. |
| 2002/0081366 A1 | 6/2002 | Cain et al. |
| 2002/0082436 A1 | 6/2002 | Jerome et al. |
| 2002/0198177 A1 | 12/2002 | Horrobin |
| 2003/0013759 A1 | 1/2003 | Das |
| 2003/0031753 A1 | 2/2003 | Watkins et al. |
| 2003/0032674 A1 | 2/2003 | Hwang |
| 2003/0045460 A1 | 3/2003 | Fogelman et al. |
| 2003/0045578 A1 | 3/2003 | Horrobin |
| 2003/0166723 A1 | 9/2003 | Nakajima et al. |
| 2004/0014810 A1 | 1/2004 | Horrobin et al. |
| 2004/0019109 A1 | 1/2004 | Owman et al. |
| 2004/0039058 A1 | 2/2004 | Ursin et al. |
| 2004/0043963 A1 | 3/2004 | Wadstein |
| 2004/0048926 A1 | 3/2004 | Hoffman et al. |
| 2004/0048927 A1 | 3/2004 | Horrobin |
| 2004/0096468 A1 | 5/2004 | Changaris |
| 2004/0102519 A1 | 5/2004 | Llewellyn |
| 2004/0162348 A1 | 8/2004 | Peet et al. |
| 2004/0171688 A1 | 9/2004 | Bar-Tana |
| 2004/0208939 A1 | 10/2004 | Sears et al. |
| 2004/0209953 A1 | 10/2004 | Wai Lee |
| 2004/0220081 A1 | 11/2004 | Kreitz et al. |
| 2004/0229950 A1 | 11/2004 | Vanderhoek |
| 2004/0248763 A1 | 12/2004 | Freeman et al. |
| 2004/0266874 A1 | 12/2004 | Akimoto et al. |
| 2005/0009779 A1 | 1/2005 | Killiaan et al. |
| 2005/0027004 A1 | 2/2005 | Kyle et al. |
| 2005/0042256 A1 | 2/2005 | Decombaz et al. |
| 2005/0123479 A1 | 6/2005 | Ferrante |

FOREIGN PATENT DOCUMENTS

| | | |
|---|---|---|
| DE | 100 29 562 | 3/2001 |
| EP | 0 505 817 A | 9/1992 |
| EP | 0 609 078 A | 8/1994 |
| EP | 0490 561 | 3/1996 |
| EP | 0 707 850 | 4/1996 |
| EP | 0 711 503 | 5/1996 |
| EP | 0 766 961 | 4/1997 |
| EP | 0 790 056 | 8/1997 |
| EP | 0 891 773 | 1/1999 |
| EP | 0 679 057 | 8/1999 |
| EP | 0 796 238 | 5/2000 |
| EP | 0 568 608 | 9/2000 |
| EP | 1 077 061 | 2/2001 |
| EP | 1 091 659 | 5/2002 |
| EP | 0 956 011 | 6/2002 |
| EP | 1 035 846 | 7/2002 |
| EP | 0 920 300 | 4/2003 |
| EP | 0 956 013 | 4/2003 |
| EP | 0 800 584 | 5/2003 |
| EP | 1 325 747 A2 | 7/2003 |
| EP | 1 325 747 A3 | 7/2003 |
| EP | 1 342 787 | 9/2003 |
| EP | 1 129 711 | 1/2004 |
| EP | 0 994 705 | 3/2004 |
| EP | 1 292 288 | 9/2004 |
| EP | 1 221 867 | 11/2004 |
| EP | 1506778 | 2/2005 |
| GB | 1 490 603 | 11/1977 |
| GB | 2 409 644 | 7/2005 |
| WO | WO 90/12080 | 10/1990 |
| WO | WO 96/05164 | 2/1996 |
| WO | WO 96/40106 | 12/1996 |
| WO | WO 97/04127 | 2/1997 |
| WO | WO 98/16215 | 4/1998 |
| WO | WO 98/44917 | 10/1998 |
| WO | WO 98/46763 | 10/1998 |
| WO | WO 98/46764 | 10/1998 |
| WO | WO 98/46765 | 10/1998 |
| WO | WO 99/51560 A1 | 10/1999 |
| WO | WO 00/09476 | 2/2000 |
| WO | WO 00/12720 | 3/2000 |
| WO | WO 00/21524 | 4/2000 |
| WO | WO 00/34791 | 6/2000 |
| WO | WO 00/40705 | 7/2000 |
| WO | WO 00/44360 | 8/2000 |
| WO | WO 00/53637 | 9/2000 |
| WO | WO 00/74669 | 12/2000 |
| WO | WO 01/10989 | 2/2001 |
| WO | WO 01/13733 | 3/2001 |
| WO | WO 01/17366 | 3/2001 |
| WO | WO 01/17524 | 3/2001 |
| WO | WO 01/97793 A | 12/2001 |
| WO | WO 01/97793 A2 | 12/2001 |
| WO | WO 02/05849 | 1/2002 |
| WO | WO 02/47493 | 6/2002 |
| WO | WO 02/092073 | 11/2002 |
| WO | WO 02/096408 | 12/2002 |
| WO | WO 02/102757 | 12/2002 |
| WO | WO 03/013276 | 2/2003 |
| WO | WO 03/013497 A | 2/2003 |
| WO | WO 03/043972 | 5/2003 |
| WO | WO 03/075003 | 9/2003 |
| WO | WO 03/075670 | 9/2003 |
| WO | WO 03/092628 | 11/2003 |
| WO | WO 2004/012753 | 2/2004 |
| WO | WO 2004/024136 | 3/2004 |
| WO | WO 2004/028529 | 4/2004 |
| WO | WO 2004/084882 | 10/2004 |
| WO | WO 2004/105517 | 12/2004 |
| WO | WO 2005/018632 A1 | 3/2005 |
| WO | WO 2005/037848 | 4/2005 |
| WO | WO 2005/063231 | 7/2005 |

OTHER PUBLICATIONS

Hoy, Carl-Erik, et al; "Absorption of γ-Linolenic Acid from Borage, Evening Primrose, and Black Currant Seed Oils: Fatty Acid Profiles, Triacylglycerol Structures, and Clearance Rates of Chylomicrons in the Rat"; *γ-Linolenic Acid: Metabolism and Its Roles in Nutrition and*

*Medicine*; AOCS Press, Champaign, IL, pp. 54-65, (1996) XP009035802.
Co-pending U.S. Appl. No. 10/567,778, filed Feb. 9, 2006.
Co-pending U.S. Appl. No. 11/791,606, filed May 25, 2007.
Co-pending U.S. Appl. No. 11/885,255, filed Aug. 29, 2007.
Akoh, C.C.; "Structured lipids—enzymatic approach"; *Inform*; vol. 6:9, pp. 1055-1061 (1995).
Bradley, D.G., "Designer fats; turning scientific advance into consumer benefit"; *Lipid Technology*; pp. 89-91, Jul. 1997.
Christensen, M.S., et al; "Intestinal absorption and lymphatic transport of eicosapentaenoic 9EPA), docosahexaenoic 9DHA), and decanoic acids: dependence on intramolecular triacylglycerol structure"; *Am. J. Clin. Nutr.* vol. 61, pp. 56-61 (1995).
Christensen, M.S., et al; "Absorption of triglycerides with defined or random structure by rats with biliary and pancreatic diversion"; *Lipids*; vol. 30, No. 6, pp. 521-526 (1995).
Decker, E.A.; "The role of stereospecific saturated fatty acid positions on lipid nutrition"; *Nutr. Rev.*; vol. 54, No. 4, pp. 108-110 (1996).
Dehesh, K., "Production of high levels of 8:0 and 10:0 fatty acids in transgenic canola by overexpression of Ch FatB2, a thioesterase cDNA from Cuphea Hookeriana"; *The Plant Journal*; vol. 9, No. 2; pp. 167-172 (1996).
Gurr, M.; "Fat digestion and assimilation"; *Lipid Technology*; pp. 94-97, Jul. 1997.
Hauumann, B.F.; "Structured lipids allow fat"; *Inform* vol. 8, No. 10, pp. 1004-1011 (1997).
Ikeda I., et al; "Lymphatic absorption of structured glycerolipds containing medium-chain fatty acids and linoleic acid, and their effect on cholesterol absorption in rats"; *Lipids*, vol. 26, No. 5, pp. 369-373 (1991).
Jandacek, R.J., et al; "The rapid hydrolysis and efficient absorption of triglycerides with octanoic acid in the 1 and 3 positions and long-chain fatty acid in the 2 position"; *Am J. Clin. Nutr.*; vol. 45, pp. 940-945 (1987).
Jensen, M.M., et al; "Intestinal absorption of octanoic, decanoic, and linoleic acids: Effect of triglyceride structure"; *Ann. Nutr. Metab*, vol. 38, pp. 104-116 (1994).
Kenler A.S., et al; "Early enteral feeding in postsurgical cancer patients"; *Annals of Surgery*; vol. 223, No. 3, pp. 316-333 (1996).
Kennedy, J.P.; "Structured Lipids: Fats of the Future"; *Food Technology*; pp. 76-83 (1991).
Kritchevsky, D. ; "Fatty acids, triglyceride structure, and lipid metabolism"; *Nutr. Biochem*, vol. 6, pp. 172-178 (1995).
Kritchevsky, D., et al; "Cholesterol vehicle in experimental atherosclerosis Part 10. Influence of specific saturated fatty acids"; *Exp. Molec. Pathol*; vol. 6, pp. 394-401 (1967).
Kritchevsky, D., et al; "Cholesterol vehicle in experimental atherosclerosis VII. Influence of naturally occurring saturated fats"; *Med. Pharmacol. Exp.*; vol. 12, pp. 315-320 (1965).
Kritchevsky, D. et al; "Cholesterol vehicle in experimental atherosclerosis Part 15. Randomized butter and randomized lard"; *Atherosclerosis*; vol. 27, pp. 339-345 (1977).
Kritchevsky D., et al; "Experimental atherosclerosis in rabbits fed cholesterol free diets. Part 10. Cocoa butter and palm oil"; *Atherosclerosis*; vol. 41, pp. 279-284 (1982).
Kritchevsky, D. et al; "Influence of triglyceride structure on experimental atherosclerosis in rabbits"; *FASEB* J 10, A187 (1996).
Kritchevsky D, Tepper SA, Kim HK, Story JA, Vesselinovitch D, and Wissler RW. 1976. Experimental atherosclerosis in rabbits fed cholesterol free diets 5. Comparison of peanut, corn, butter and cocon ut oils. Exp. Molec. Pathol. 24: 375-391.
Kritchevsky, D., et al; "Influence of triglyceride structure on experimental atherosclerosis in rabbits"; *FASEB* J 9, A320 (1995).
Kritchevsky,k D., et al; "Thyroid hormone and experimental atherosclerosis in rabbits"; *Atherosclerosis*; vol. 23, pp. 249-252 (1976).
Kubow, S., et al; "The influence of positional distribution of fatty acids in native, interesterified and structure-specific lipds on lipoprotein metabolism and atherogenesis"; *Nutr. Biochem*; vol. 7, pp. 530-541 (1996).
Mattson, F.H., et al; "The digestion and absorption of triglycerides"; *J. Biol. Chem.*; vol. 239, pp. 2772-2777 (1964).

Metolli, A.M., et al; "Medium-chain lipds: new sources, uses"; *Inform*; vol. 8, No. 6, pp. 597-603 (1997).
Myher, J.J., et al; "Acylglycerol Structure of peanut oils of different atherogenic potential"; *Lipids*; vol. 12; pp. 765-878 (1977).
Sadou, H. et al; "Differential incorporation of fish-oil eicosapentaenoate and docosahexaenoate into lipds of lipoprotein fractions as related to their glycerol esterification: a short-term (postprandial) and long-term study in healthy humans"; *Am J. Clin Nutr.*; vol. 62, pp. 1193-1200 (1995).
Small, D.M.; "The effects of glyceride structure on absorption and metabolism"; *Annu. Rev. Nutr.*; vol. 11, pp. 413-434 (1991).
Voelker, T.A., et al; "Fatty acid biosynthesis redirected to medium chains in transgenic oilseed plants"; *Science*; vol. 257, pp. 72-74 (1992).
Zock, P.L., et al; "Positional distribution of fatty acids in dietary triglycerides: effects on fasting blood lipoprotein concentrations in humans"; *Am. J. Clin. Nutr.*; vol. 61, pp. 48-55 (1995).
Kritchevsky, D.; "Fatty acids, triglyceride structure, and lipid metabolism"; *Nutr. Biochem*; vol. 6, pp. 172-178 (1995).
Miles, E.A., et al; "The influence of different combinations of γ-linolenic acid, stearidonic acid and EPA on immune function in healthy young male subjects"; *British Journal of Nutrition*; vol. 91, pp. 893-903 (2004).
McCormick, J.N., et al; "Immunosuppressive effect of linolenic acid"; *The Lancet*; p. 508 (1977).
Demmelmair, H., et al; "Influence of formulas with borage oil or borage oil plus fish oil on the arachidonic acid status in premature infants"; *Lipids*, vol. 36, No. 6; pp. 555-566 (2001).
Thijs, C., et al; "Essential fatty acids in breast milk of atopic mothers: comparison with non-atopic mothers, and effect of borage oil supplementation"; *European Journal of Clinical Nutrition*; vol. 54, pp. 234-238 (2000).
Leventhal, L.J., et al; "Treatment of Rheumatoid Arthritis with Blackcurrant Seed Oil"; *British Journal of Rheumatology*; vol. 33, pp. 847-852 (1994).
Zurier, R.B., et al; "Gamma-Linolenic Acid Treatment of Rheumatoid Arthritis"; *Arthritis & Rheumatism*; vol. 39, No. 11, pp. 1808-1817 (1996).
Patent Abstracts of Japan, vol. 1995, No. 01, Feb. 28, 1995 & JP 06 279311 A (Sagami Chem Res Center; others: 01), 04 Oct. 4, 1994 (Abstract).
Patent Abstracts of Japan, vol. 1996, No. 03, Mar. 29, 1996 & JP 07 309773 A (Sagami Chem Res Center; others: 01), Nov. 28, 1995 (Abstract).
Mechoulam, R., et al; "Cannabinoids and brain injury: therapeutic implications"; *Trends in Molecular Medicine*; vol. 8, No. 2; pp. 58-61 (2002) XP-002381881.
Database Biosis (Online), Biosciences Information Service, Philadelphia, PA, USA; Mar. 2003; Rockwell C.E., et al; "Inhibition of interleukin-2 (IL-2) by the endogenous cannabinoid, 2-arachidonyl glycerol, is partly mediated through peroxisome proliferators-activated receptor-gamma (PPAR-gamma)"; Database accession No. PREV200300230725 abstract & *Toxicological Sciences*, vol. 72, No. s-1, Mar. 2003, p. 328, 42$^{nd}$ Annual Meeting of the Society of Toxicology; Salt Lake City, UT, USA; Mar. 9-13, 2003, ISSN: 1096-6080.
Database Embase (Online) Elsevier Science Publishers, Amsterdam, Nl; 2005, Kaplan, B. L.F., et al; "2-Arachidonoyl-glycerol suppresses interferon-γ production in phorbol ester/ionomycin-activated mouse splenocytes independent of CB1 or CB2", XP-002381886 (abstract); *Journal of Leukocyte Biology*; vol. 77 pp. 966-974 (2005).
Ouyang, Y., et al; "Suppression of Interleukin-2 by the Putative Endogenous Cannabinoid 2-Arachidonyl-Glycerol is Mediated through Down-regulation of the Nuclear Factor of Activated T Cells"; *Molecular Pharmacology*; vol. 53, pp. 676-683 (1998) XP-002381882.
Venderova, K., et al; "Differential effects of endocannabinoids on [$^3$H]-GABA uptake in the rat globus pallidus"; *Experimental Neurology*; vol. 194, pp. 294-287 (2005).
Fisher, B.A.C., et al; "Effect of omega-6 lipid-rich borage oil feeding on immune function in healthy volunteers"; *Biochemistry Society Transactions*; vol. 25; p. 343S (1997).

Wahl, S.M.; "Transforming Growth Factor β: The Good, the Bad, and the Ugly"; *The Journal of Experimental Medicine*, vol. 180; pp. 1587-1590 (1994).

Levin, G., et al; "Differential metabolism of dihomo-γ-linolenic acid and arachidonic acid by cyclo-oxygenase-1 and cyclo-oxygenase-2: implications for cellular synthesis of prostaglandin $E_1$ and prostaglandin $E_2$"; *Biochem. J.*; vol. 365; pp. 489-496 (2002).

Leventhal, L.J., et al; "Treatment of Rheumatoid Arthritis with Gammalinolenic Acid"; *Annals of Internal Medicine*; vol. 119; No. 9; pp. 867-873 (1993).

Fig.6.

Effect of Ratio of Linoleic Acid to Gamma-Linolenic Acid on Acute Phase of SCH Induced CREAE in Biozzi AB/H Mice

| 18:2n-6/18:3n-6 | Incidence of EAE |
| --- | --- |
| 0.5 | 0/10 |
| 1.5 | 4/10 |
| 7.5 | 7/10 |
| Controls | 10/10 |

USE OF TRIGLYCERIDE OILS CONTAINING γ-LINOLENIC ACID RESIDUES AND LINOLEIC ACID RESIDUES FOR THE TREATMENT OF NEURODEGENERATIVE DISEASE

This application is the U.S. National Phase of International Application PCT/GB04/002089, filed 14 May 2004, which designated the U.S. PCT/GB04/002089 claims priority to British Application No. 0311081.4 filed 14 May 2003, and U.S. Provisional Application No. 60/497,332 filed 25 Aug. 2003. The entire content of these applications are incorporated herein by reference.

The present invention relates to a method for treating neurodegenerative conditions, particularly those in which increase in transforming growth factor β (TGF-β) is beneficial, particularly TGF-β1. More particularly the present invention provides treatment for conditions such as multiple sclerosis and the degenerative sequelae associated with head trauma, stroke and intracranial bleeds, whereby neuronal function is improved or restored from an impaired condition. Further provided are novel use of known and novel compounds comprising unsaturated fatty acid moieties for the manufacture of medicaments capable of effectively treating such conditions, more particularly being capable of achieving previously unattained levels of success with regard to recovery of neurological function.

BACKGROUND OF THE INVENTION

It is well reported in the literature that essential fatty acids (EFAs) of the n-3 and n-6 unsaturation pattern have beneficial effect in a wide variety of human physiological disorders. WO 02/02105 (Laxdale Limited) describes their beneficial use for an extremely wide range of diseases and as a general nutritional supplement. Harbige (1998) Proc. Nut. Soc. 57, 555-562 reviewed the supplementation of diet with n-3 and n-6 acids in autoimmune disease states, and particularly noted evidence of benefit of γ-linolenic (GLA) and/or linoleic acid (LA) rich oils, such as borage oil, in reducing clinically important signs and symptoms of rheumatoid arthritis.

Two studies on multiple sclerosis (MS) patients are noted that indicate that relapse and severity of the disease might be reduced by treatment with oils containing n-6 acid moieties (Miller et al (1973) and Bates et al (1978)), but a further study failed to confirm this effect (Paty et al (1978)). These papers report that supplementation of human patients with about 20 g/day of linoleic acid (18:2n-6) affected duration and severity of relapses of multiple sclerosis such that relapses were less frequent, less severe and of shorter duration than controls. Bates noted that a mixture of linoleic acid and γ-linolenic acid had been suggested back in 1957 to be possibly more efficacious in treating inflammation and autoimmune diseases and set out to investigate this in the trial. However, it was found that where this combination was tried, at 3 g oil per day (Naudicelle Evening Primrose oil) patients who had relapses became more ill on the trial oil than on the control.

Meta analysis of these linoleic acid studies by others (Dworkin et al (1984)) demonstrated reduced relapse rate and severity with a decrease in the degree of long-term progression of the disease in patients with mild multiple sclerosis. Later open studies of patients with multiple sclerosis suggest that low fat diet and/or manipulation of dietary n-3 and n-6 fatty acids may be beneficial (Swank & Grimsgaard (1988); Harbige et al (1990).

Although the aetiology of MS remains unknown, strong evidence suggests the presence of autoimmune mechanisms in the disease pathogenesis [Martino & Hartung 1999]. Studies have shown that MS patients have a much higher number of neuro-antigen e.g. myelin basic protein (MBP) and myelin oligodendrocyte glycoprotein (MOG) autoreactive T-cells which are in an increased state of activation compared with healthy controls [Fredrikson et al 1994, Kerlero de Rosbo et al 1993, 1997, Chou et al 1992, Ota et al 1990, Burns et al 1999, Zhang et al 1994, Tejada-Simon et al 2001]. The actual processes of axonal damage e.g. chronic inflammation, demyelination and astrogliosis in MS is complex but white matter inflammation and demyelination are considered to determine disease severity, whilst recent studies suggested that axonal damage in MS begins in the early stages of the disease and contributes to disability (De Stefano et al, 2001).

Experimental autoimmune encephalomyelitis (EAE) is the most frequently used animal model for immune mediated effects of MS. Studies in the guinea-pig have shown that linoleic acid partially suppresses the incidence and severity of EAE (Meade et al (1978)). Using γ-linolenic acid-rich oils from fungal or plant sources, complete protection was demonstrated in both rats and mice (Harbige et al (1995), 1997b). These investigations demonstrated disease modifying effects of linoleic acid and γ-linolenic acid on clinical and histopathological manifestations of EAE. Depending on dose, γ-linolenic acid was fully protective in acute rat EAE whereas linoleic acid had dose-dependent action on the clinical severity but did not abolish it.

Despite these experimental findings, it is recognised that the human disease, multiple sclerosis, is highly complex and can be conversely exacerbated and ameliorated by the activity of T-cells and other immune response factors. It is thought that the n-6 fatty acids promote autoimmune and inflammatory disease based upon results obtained with linoleic acid only. TGF-β and $PGE_2$ production has been shown to be increased non-specifically in γ-linolenic acid fed mice ex vivo; but whilst TGF-β has been reported to protect in acute and relapsing EAE ((Racke et al (1993); Santambrogio et al (1993)), PG inhibitors such as indomethacin augment, and thus worsen, the disease (Ovadia & Paterson (1982)).

Cytokines are implicated in the pathogenesis of MS, with many studies showing an increase in myelinotoxic inflammatory cytokines (TNF-α, IL-1β and IFN-γ) coinciding with the relapse phase of the disease. Conversely, levels of the antiinflammatory and immunosuppressive cytokine transforming growth factor-beta1 (TGF-β1) appear to be reduced during a phase of relapse and increase as the patient enters remission. Thus the balance between biologically active TGF-β1 and the pro-inflammatory TNF-α, IL-1β and IFN-γ appears to be dysregulated during MS relapse-remission.

During natural recovery phase from EAE, TGF-β-secreting T-cells inhibit EAE effector cells, TGF-β is expressed in the CNS and, in oral-tolerance-induced protection in EAE, TGF-β and $PGE_2$ are expressed in the brain (Karpus & Swanborg (1991); Khoury et al (1992)). Harbige ((1998) concluded that dietary γ-linolenic acid effects on EAE are mediated through $Th_3$-like mechanisms involving TGF-β and possibly through superoxide dismutase antioxidant activity.

It has been suggested to use, inter alia, γ-linolenic acid and linoleic acid rich Borage oil as a means to provide immunosuppression in multiple sclerosis (U.S. Pat. No. 4,058,594). The dose suggested is 2.4 grams of oil per day and no actual evidence of efficacy is provided.

Borage oil (typically 23% γ-linolenic acid and 37% linoleic acid per 100% fatty acid content) has been shown to significantly reduce clinically important signs and symptoms of autoimmune disease associated with active rheumatoid arthritis (Leventhal et al (1993)). Borage oil and fungal oil (see FIG. 1) have been shown to be effective in the EAE animal model use to identify MS candidates, whilst never having been shown to be significantly effective in the human disease. High levels of linoleic rich oil containing low levels of γ-linolenic acid (EPO: linoleic acid:γ-linolenic acid 7:1) partially suppressed the incidence and severity of EAE in rat (Mertin & Stackpoole, 1978) whereas the Naudicelle study referred to above led to worsening of patients. In spite of the use of Borage oil and other GLA/LA containing oils such as Evening Primrose oil by multiple sclerosis sufferers over the past 30 years or so, the vast majority of patients fail to recover from the disease, showing no significant improvement, with the underlying disease continuing to progress to death.

Other more dramatic immunosuppressant treatments, including T cell depleters and modulators such as cyclophosphamide, are also shown to be effective in the EAE model, but where these are employed in the human multiple sclerosis disease symptoms improve, but the underlying disease continues to progress. T-cells indeed produce beneficial cytokines, such as TGF-β1, as well as deleterious ones in man. David Baker of Institute of Neurology, UK summed up the disparity between what is effective in the EAE and in MS with a paper entitled 'Everything stops EAE, nothing stops MS' at the 10<sup>th</sup> May 2004 UK MS Frontiers meeting of the UK MS Society.

It is clear that immunosuppression alone cannot cure MS. This is almost certainly due to a fundamental underlying metabolic disorder in MS patients that leads to membrane abnormality, cytokine dysregulation and subsequent immune attack and lesioning. Although patients go into remission in relapse-remitting disease, the underlying demyelination proceeds.

The 'gold standard' treatment for MS remains interferon, such as with β-Avonex®, Rebif® and other interferon preparations. This gold standard treatment only addresses needs of some, eg 30%, of the patients and even in these symptom improvement is restricted to reduced severity of relapses. Whilst symptoms may be reduced in a proportion of patients, the disease tends to progress to further disability and death due to underlying degeneration.

SUMMARY OF THE INVENTION

The present inventors have now surprisingly determined that with compliance to a 'high dose' treatment with triglyceride oil containing γ-linolenic acid with suitable accompanying fatty acid content, remarkable levels of improvement in almost all symptoms of MS can be achieved, way surpassing that provided by the present gold standard treatment. Such success is particularly surprising in the light of the prior use of other γ-linolenic acid containing preparations without such significant success.

Over an 18-month period, patients taking high dose selected borage oil showed significant ($p<0.001$) and marked improvements in EDSS score, a reduced rate of relapse, symptomatic relief of muscle spasticity and painful sensory symptoms, and improved objective measures of cognitive functions. Low dose borage oil was without effect.

Patients taking high dose borage oil maintained their level of peripheral blood mononuclear cell production (PBMC) of TGF-β1 during the trial period, their pro-inflammatory cytokines TNF-α and IL-1β were significantly and markedly (<70%) reduced and they either maintained or increased the PBMC membrane long chain omega-6 fatty acids dihomo-γ-linolenic acid (DHLA) and arachidonic acid (AA) in contrast to patients taking placebo who demonstrated loss of these fatty acids over the course of the trial period.

This whilst immuno-suppression would be expected to reduce active lesioning and neurodegeneration, the present treatment has apparently targeted maintenance of key membrane lipid components that are otherwise specifically lost in MS, suggesting a correction of a metabolic defect not otherwise effectively treated by current therapies. The fact that the low dose (5 grams/day) had no effect on this supports such determination.

Particularly the inventors have determined that a triglyceride oil comprising triglycerides of both γ-linolenic acid and linoleic acid with specific positional distribution within the triglyceride molecules, preferably with oleic acid, can provide significant decreasing EDSS score in multiple sclerosis patients over a number of months and years, a result that is unattainable with any of the currently administered therapies.

γ-Linolenic acid (18:3n -6, GLA) is known to be rapidly converted to longer-chain omega-6 polyunsaturated fatty acids dihomo-γ-linolenic acid and arachidonic acid in vivo (Phylactos et al 1994, Harbige et al 1995, 2000). Therefore to increase the level of membrane long chain omega-6 fatty acids in MS the inventors have reviewed results obtained with several GLA-containing oils:- both fungal (from *Mucor javanicus*) and plant (*Borago officinalis*), Evening primrose *Oenothera* spp. or Blackcurrant *Ribes* spp) as well as a synthetic tri-GLA oil as GLA delivery systems in an in vivo experimental animal model of MS known as chronic relapsing experimental autoimmune encephalomyelitis (CREAE).

Experimental autoimmune encephalomyelitis (EAE) is an autoimmune inflammatory disease of the CNS, with or without demyelination, inducible in rodents and other mammalian species. Induction of EAE in rats however (using guinea pig basic protein), does not produce histological features of demyelination (Brosnan et al 1988) but induces an acute mono-phasic disease pattern, unlike MS which is characterised by CNS demyelination and is clinically relapsing-remitting. Chronic relapsing and demyelinating EAE models (CREAE), which are characterised by demyelination and relapse phases, are therefore currently the animal models of choice for MS research (Fazakerley 1997). With the demonstration that myelin oligodendrocyte glycoprotein (MOG) is an important neuroantigenic target in MS (Genain et al 1999) and the demonstration of far greater responses of peripheral blood auto-reactive lymphocytes to this neuroantigen, compared with MBP, in MS (Kerlero de Rosbo et al 1993, 1997) MOG induced CREAE has become the animal model of choice with features closely resembling those observed in MS (Fazakerely et al 1997, Genain et al 1999, Amor et al 1994).

Based on the results of these experiments two key selection criteria were adopted for selection improved lipid compounds for achieving the current aims. Evidence from CREAE and rat EAE feeding studies indicates that an enriched blackcurrant seed oil (72% w/w 18:3n-6, GLA) did not protect against EAE (see Table 3). Importantly blackcurrant seed oil has a low sn-2 GLA with most of the GLA in the sn-1 and sn-3 positions (Lawson and Hughes 1988). Furthermore a structured triacylgcerol containing three GLA's (TG-GLA) provided protective effects similar to that of the borage oil used in CREAE (Table 2). This would also be consistent with the sn-2 GLA being important i.e. the outer pair sn-1 and sn-3 GLA being enzymatically removed in vivo and probably undergo oxidation leaving the sn-2 GLA only. This selective hydrolysis arises from the known ability of specific lipases to remove the sn-1 and sn-3 fatty acids from triacylgcerol molecules but an apparent protection of the sn-2 position in vivo (Lawson and Hughes 1988, Kyle 1990).

The inventors' review of this data also indicates that the ratio of linoleic acid (LA) to γ-linolenic acid (GLA) residues may be a key efficacy feature of oils containing LA and GLA in the CREAE model of MS (Table 1). Table I shows the compositional analysis and efficacy in CREAE of fungal oil, borage oil, evening primrose oil and safflower oil. The most effective treatment in reducing the incidence of CREAE was fungal oil with an LA:GLA ratio of 0.85. Borage oil was also very effective with an LA:GLA ratio of 1.5. Furthermore, experiments with a structured triglyceride containing GLA at sn-1, sn-2 and sn-3 (TG-GLA) demonstrated GLA to be an active component. Moreover TG-GLA was also effective at a lower dose level than the borage oil (see Table 2).

Different Borage seed oil's also appear to vary in their level of sn-2 GLA e.g. 10% sn-2 GLA (Liu et al 2000) and 40% sn-2 (Lawson and Hughes 1988) which is consistent with our unpublished observations of sn-2 GLA (range 38-46%) and possibly the failure of some borage oils to produce fully protective effects in CREAE, although other factors such as antioxidant composition may also be important (unpublished). Borage oils having as much as 60% sn-2 GLA have been reported (Huang and Mills (1996) γ-Linolenic acid: metabolism and Its Roles in Nutrition and Mediceine: Chapter 6) and noted to be effective at getting GLA into lymph.

Table 3 of EP 0520624 (Efamol Holdings) compares the triglyceride content of Evening Primrose and Borage Oils, the former being taught to be more therapeutically effective than the latter for a variety of GLA responsive disorders. This document indicates Borage oil to have twenty seven different trigyceride components, only 20% of which have sn-2 GLA. Page 3, lines 40-42 notes that biological testing has shown that equal amounts of GLA may indeed have very different effects when that GLA is supplied as different oil sources. Crucially, it then directs the reader to one particular fraction present in Evening Primrose Oil (EPO), but not Borage Oil, as being responsible for the former's superior effect in raising PGE1 (see EP 0520624 Chart page 4 and Table 2) and thus anti-inflammatory effect: that fraction being di-linoeoyl-mono-gamma-linolenyl-glycerol (DLMG) which it states to be 18 to 19% of the total triglyceride in EPO. Page 6 clearly teaches that the position of the GLA, in sn-1, 2 or 3, is not important to this effect.

Dines et al (1994) Proceedings of the Physiological Society, Aberdeen Meeting 14-16 September 1994 report on studies treatment of diabetic neuropathy neuronal damage with γ-linolenic acid containing oils of the type advocated by EP 0520624 and again note that Borage Oil was not very effective in treating this neurodegeneration whereas Evening primrose oil was. The paper concludes that Boage Oil contains other constituents that interfere with GLA activity.

In contrast to this prior art, the present inventors used a borage oil that was selected with the highest sn-2 GLA for trial purposes (>40%)—compared with lower amounts in other samples that were available at the time. Blackcurrant seed oil, which at the time was available in relative large quantities was not considered optimal because of it's low sn-2 GLA content.

A further selection criterion was that the level of total long chain monoenoic fatty acids be kept below 5%. There was a significant level of erucic acid (22:1n-9) i.e. 1.4-2.38% of the total fatty acids, and other long chain monoenoic fatty acids i.e. 24:1n-9 (nervonic acid) and 20:1n-9 (gadoleic acid) in different borage seed oil (*Borago officinalis*) samples from different sources (Table 4).

Additionally because of potential impact on absorption, metabolism and immune functions of vitamin E (Harbige 1996, 2003), the trial oil contained only natural levels of vitamin E (0.05 mg/g) with no additionally added vitamin E as is routinely the case with commercial borage seed oils (e.g. 1 mg/g).

It is believed that such selected oils have an immunosuppressant effect, but significantly also have and a metabolic supplementation effect that has benefit in reducing immune attack on lesions whilst creating the conditions necessary for their repair, something that has not been achieved with any medication previously provided for MS.

In a first aspect of the present invention there is provided a method of treating a patient in need of therapy for a neurodegenerative disease comprising administering to that patient a therapeutically effective dose of an oil containing both γ-linolenic acid and linoleic acid residues as triglyceride ester, the ratio of γ-linolenic acid to linoleic acid residues at the sn-2 position of the triglyceride being at least 0.8; the amount of γ-linolenic acid residues at the sn-2 position being at least 18%, wherein the oil is administered at a dose sufficient to maintain or elevate TGF-β levels in the patient to therapeutic levels.

By therapeutic levels is meant levels at least consistent with healthy subjects. Preferably the dose is such as to produce a TGF-β1/TNF-α ratio in blood of a patient, after 18 months of daily dosing, of 0.4 to 3.0, at least 0.5, more preferably at least 0.75 and most preferably at least 1. Preferably the dose is such as to produce a TGF-β1/IL-1β ratio in blood of a patient, after 18 months of daily dosing, of at least 0.5, more preferably at least 0.75 and most preferably at least 1. Preferably said levels are produced after 12 months and more preferably after 6 months.

Typically the amount of oil administered daily will be between 3 and 30 grams, orally dosed, still more preferably between 5 and 20 grams and most preferably between 7 and 18 grams, typically 15 grams.

Most preferably, in addition to the γ-linolenic acid and linoleic acid fatty acid residues, the oil includes an esterified fatty acid that is non-structural, ie. that is metabolised to produce energy, such as oleic acid residues. By residue is meant the moiety that remains after the fatty acid carboxyl group esterifies to one of the hydroxy groups of the glycerol molecule.

Most preferably the oil administered is an oil source from Borage oil or a fungal oil eg. eg from *Mucor javanicus*, Typical Borage oil and fungal oil compositions are illustrated in Table 1 wherein 18:2n-6 and 18:3n-6 represent linoleic and γ-linolenic acid residue by percent respectively.

Typically Borage oils contain from 20 to 25% γ-linolenic acid residues as percentage of fatty acid residues in the oil and from 35 to 40% linoleic acid residues. Preferred Borage oils are those in which the amount of esterified γ-linolenic acid at the sn-2 position is at least 35% of fatty acid residues at that position, more preferably greater than 39% and still more preferably greater than 40%. Most preferred oils are over 41%, such as 42 to 44% sn-2 GLA, whilst ideally they will be over 45%. As stated by Huang et al above, 60% sn-2 GLA Borage Oils have been produced and should be available for selection. The sn-1 and sn-3 position residues are preferably linoleic, oleic and γ-linolenic acid residues, with preferred oils having relatively high oleic acid content in at least one, if not both, of these positions, eg, in excess of 12%, more preferably in excess of 14%.

A typical Borage oil suitable for use in the use of the present invention has fatty acid distribution as follows Sn-1: 14% 18:1 (Oleic), 54% 18:2n-6 (linoleic) and 4% 18:3n-6 (γ-linolenic)

Sn-2: 14% 18:1 (Oleic), 42% 18:2n-6 (linoleic) and 40% 18:3n-6 (γ-linolenic)

Sn-3: 19% 18:1 (Oleic), 18% 18:2n-6 (linoleic) and 30% 18:3n-6 (γ-linolenic)

Where a fungal oil is use, such as from *Mucor* species, the total amount of γ-linolenic acid residues may be lower than for Borage oil as long as the sn-2 γ-linolenic acid:linoleic acid ratio is at least 0.8, more preferably greater than 1. This is because fungal oils tend to have more 'metabolic' directed oleic acid residues than linoleic acid residues. Thus preferred fungal oils are those in which the amount of esterified γ-linolenic acid at the sn-2 position is at least 18% of fatty acid residues at that position, more preferably at least 20% and most preferably at least 22%. Preferred fungal oils have in excess of 45% of the sn-2 fatty acid residues as oleic acid residues, more preferably in excess of 50%.

Sn-1: 25% 18:1 (Oleic), 5% 18:2n-6 (linoleic) and 13% 18:3n-6 (γ-linolenic)

Sn-2: 54% 18:1 (Oleic), 19% 18:2n-6 (linoleic) and 20% 18:3n-6 (γ-linolenic)

Sn-3: 40% 18:1 (Oliec), 3% 18:2n-6 (linoleic) and 20% 18:3n-6 (γ-linolenic)

It will be realised by those skilled in the art that such oils will need to be sourced by testing for the percentage of said fatty acids at each position as an average over the many triglycerides in a give oil mix. Such is well within the skill of those in the art, such as eg. Mylnefiled Research Services Ltd, Lipid Analysis Unit, Mylnefiled, Inverghowrie, Dundee DD2, 5DA, Scotland UK. The applicants have managed to source a number of such oils meeting the criteria set out above, the highest sn-2 figures of about 46% being found for example in New Zealand sourced oils in 2003: this of course may vary from year to year. It is important, however, given the lack of response with the low dose (5 g/day) Borage Oil that a patients efforts to recover are not undermined by the equivalent of underdosing by provision of a lower sn-2% GLA Borage Oil than the daily dose requires.

A further NMR method for analysis of such oils in a selection process is provided in the methods section below. It will however be realised that should all oils available at a given time be below the 35% sn-2 GLA figure, and preferably if they are below 40 or 45%, supplementation with a synthetic triglyceride or tryglyceride mix will be possible. A number of suitable lipids are known in the art and may for example be isolated or combined mixtures of LGL, OGO, OGL, LGO or other components known to be present in Borage Oil (see Table 3 of EP 0520624). Even TriGLA might be added (FR 2,617,161 (1988)), although it is preferred for the present purposes to keep the sn-1 and sn-2 position GLA levels from getting too high as that would run the risk of overly pro-inflammatory effect due to overflow into systemic GLA and thus DHGLA and then Arachidonic pools. Synthesis of OGO is for example taught in Y.-S. Huang, X. Lin, P. R. Redden and D. F. Horrobin, *J. Am. Oil Chem. Soc.*, 72, 625-631 (1995) In vitro Hydrolysis of Natural and Synthetic γ-Linolenic Acid-Containing Triacylglycerols by Pancreatic Lipase and K. Osada, K. Takahashi, M. Hatano and M. Hosokawa, *Nippon Suisan Gakkaishi.*, 57, 119-125 (1991). Chem. Abs. 115: 278299 Molecular Species of Enzymically-synthesized Polyunsaturated Fatty acid-rich Triglycerides.

For treatment regimes where high amounts of any of these high Sn-2 GLA oils are administered it is recommended that the amount of potentially toxic long chain monoenoic fatty acids, such as erucic acid (22: 1n-9) and other long chain monoenoic fatty acids i.e. 24:1n-9 (nervonic acid) and 20:1n-9 (gadoleic acid), are as low as possible, preferably lower than 5% of fatty acid residues, more preferably less than 3% and more preferably less than 2%.

Another feature of a preferred oil is low or zero added vitamin E such that only natural levels of vitamin E (0.05 mg/g) is provided.

Further aspects of the present invention provide use of triglyceride oils as described above for the manufacture of a medicament for the treatment of neurodegenerative disease, more specifically for the arresting of underlying neurodegeneration and the restoration of neuronal function. Particularly such medicaments are for the normalising of neuronal membrane composition, the restoration of healthy TGF-β1/TNFα ratios and the ratios of TGF-β1 with other cytokines, the arresting of neurodegeneration in multiple sclerosis and the restoration, in part or completely, of neuronal function such as measured, eg. By MRI or CAT scan or by EDSS score. Such use will include treatment of cerebral impairment after stroke, head trauma and intracranial bleeding.

Also provided are selected triglyceride oils having particular efficacy in treating multiple sclerosis and effecting beneficial changes in ratio of cyctokines in vivo, these oils eing those set out as preferred for the method described above.

The oils for use in the present invention may be administered by any of the conventional vehicles known in pharmacy. Most conveniently they are administered as neat oils or in admixture with foodstuffs, in the form of capsules containing such oils, or in enterically coated forms. Other forms will occur to those skilled in the art as delivery technology advances.

It will be realised by those skilled in the art that other beneficial agents may be combined with the oils for use in the present invention. These might be ion channel blockers, eg. sodium channel blockers, interferons, T-cell depleters, steroids or other palliative agents. It will further be realsied that where the immune and inflammatory responses are being modulated, such combinations will need to be made carefully, given the complex nature of these systems. However, given the delayed response to the present oils, shorter acting agents might be beneficial in the first months of treatment before the TGF-β1 levels are normalised, as long as the additional treatment does not impede this normalization process.

The present invention will now be described by way of Example only by reference to the following non-limiting Tables, Examples and Figures. Further embodiments falling within the scope of the invention will occur to those skilled in the art in the light of these.

Tables

Table 1: Shows the compositional % Total fatty acid content of various triglyceride oils and protective effect in EAE.

Table 2: Shows the parameters of the three treatment groups in high sn-2 GLA Borage Oil trial Table 3: Shows the effect of various forms of GAL on EAE incidence and clinical score in SJL mice.

Table 4: Shows the failure of enriched Blackcurrent oil, a high GLA, but low sn-2 -GLA, plant oil, to match fungal and Borage oils in EAE.

Table 5: Shows the results analyses of four batches of trial Borage Oil particularly with respect of monoenes.

Table 6: Shows an analysis of a non-trial oil particularly with respect to monoenes.

BRIEF DESCRIPTION OF THE DRAWINGS

Figures

FIG. 6: Shows the effect of linoleic acid:γ-linolenic acid ratio of oils as compared to their protective effect on mice CREAE.

METHODS

Figure 1:
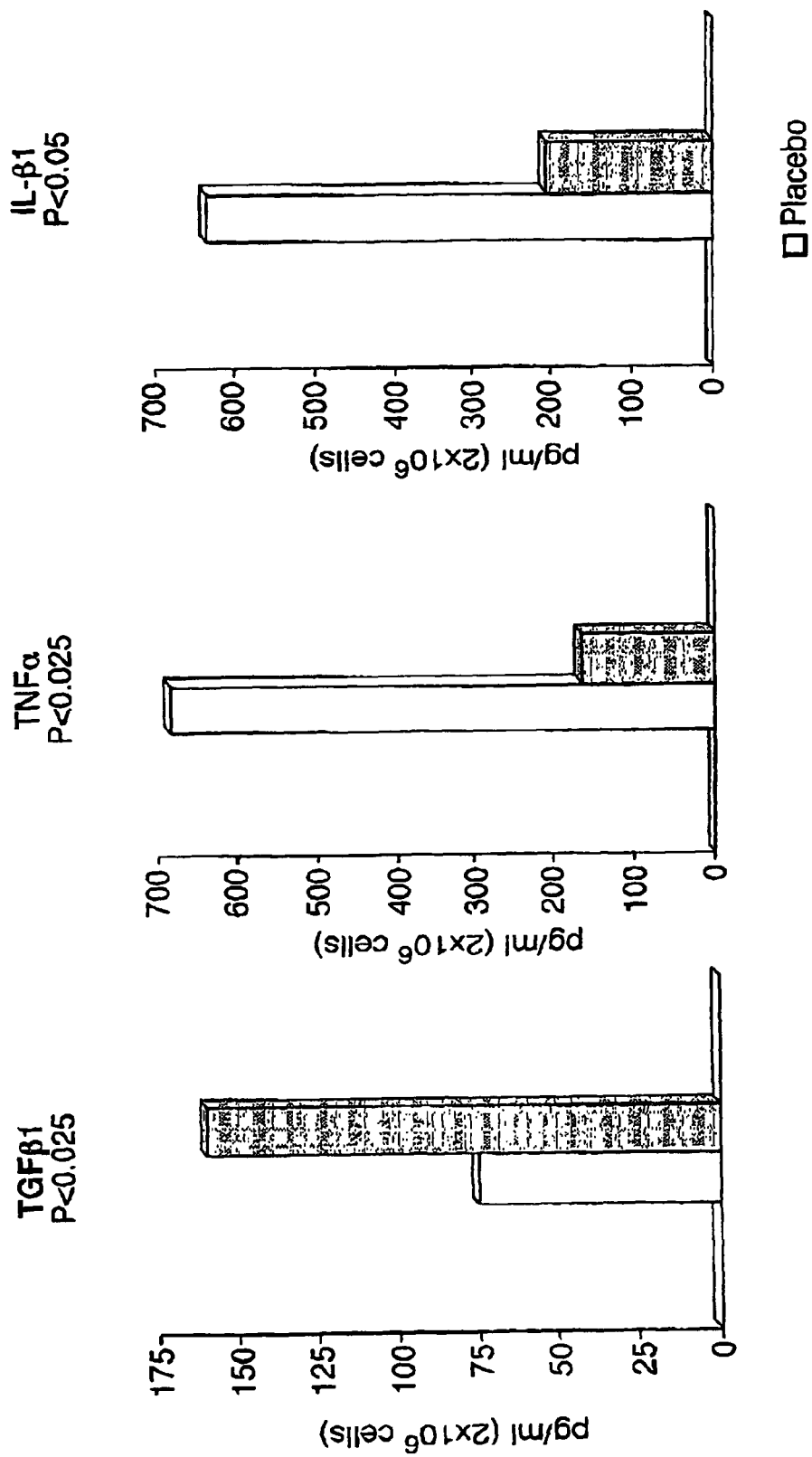
FIG. 1: Shows peripheral blood mononuclear cell cytokine production in placebo and trail oil treated human MS patients at 18 months.

Positional Analysis of Gamma-linolenic acid (GLA) in Borage oil Samples by Quantitative-$^{13}$C-NMR Analytical methodologies for the determination of fatty acid composition and positional distribution in triacylglycerols generally require hydrolysis of the triacylglycerols by enzymes or chemical processes and subsequent analysis of the mono-and diacylglycerol components by chromatographic techniques. These methods are destructive and do not allow the recovery of the original samples. The hydrolysis procedure usually gives rise to some acyl migrations, resulting in substantial errors of the positional distribution.

There are several properties of $^{13}$C nuclear magnetic resonance (NMR) that make its application to positional analysis useful. First, the chemical shift is sensitive to the molecular structure, thereby giving rise to a spectrum where each nucleus is identified by a peak at a specific frequency. The resolution of the nuclei in each environment is determined by the linewidth and the chemical shift differences between adjacent peaks. Second, the area under the peak, arising from each nucleus, is proportional to the number of nuclei in that environment because all $^{13}$C exhibit the same absorption. Therefore, the chemical shift and the integrated area of each peak can be used for both qualitative and quantitative measurements of each nucleus. Thirdly, the preparation of the sample for this application is simple. Finally, NMR is a non-destructive technique that allows the sample to be recovered for other purposes. $^{13}$C NMR methods are normally based on analysing the cluster of signals for the carbonyl carbons. Two clusters of signals are normally observed corresponding to acids in the sn 1,3- and 2-positions. They are usually readily distinguished since the two environments give rise to a separation of about 0.4 ppm. Within each of these two clusters, there must be separate signals for each acid or groups of acids. This criterion is most easily met when the acids have carbon-carbon double bonds (i.e. are unsaturated) close to the carboxyl group e.g. n=4, 5 or 6. The carbonyl carbon signals from acids of the same double bond group (e.g. EPA and AA) will not normally be distinquished. Such methods seemed to be valuable for analysing GLA-containing triacylglycerols and this proved to be the case.

REFERENCES

M. M. Bergana and T. W. Lee, *J. Am. Oil Chem. Soc.*, 73, 551-556 (1996) G. Vlahov, *Magn. Reson. Chem.*, 36, 359-362 (1998)

EXPERIMENTAL

Materials/Sample-preparation

Monoacidtriacylglycerols were purchased from Sigma Chemicals and Nu-Chek-Prep Inc:

| | |
|---|---|
| Tripalmitin | (Tri-16:0) |
| Tristearin | (Tri-18:0) |
| Triolein | (Tri-18:1n-9) |
| Trilinolein | (Tri-18:2n-6) |
| Trigammalinolenin | (Tri-18:3n-6) |
| Trieicosenoin | (Tri-20:1n-9) |
| Trierucin | (Tri-22:1n-9) |
| Trinervonin | (Tri-24:1n-9) |

Approx 180 mg of lipid in 700 μL of deuteriochloroform was used throughout the study.

$^{13}$C-NMR-data

The proton-decoupled $^{13}$C NMR data with suppressed NOE were collected at 21° C. in a 5-mm broadband probe on a Jeol 500 MHz spectrometer operating at 125.728 MHz. Waltz decoupling was the chosen mode of decoupling and was gated on only during the 14.89 s acquisition time. The relaxation delay was set at 30 secs and the pulse angle was 90°. The spectral window used was ca. 35 ppm (from 173.5 to 172.6 ppm) with a 170 ppm offset. The spectra were internally referenced to CDCl$_3$ at 77.0 ppm. Typically, the approximate number of scans collected for adequate signal-to-noise ranged from 300 to 1200 scans, depending on the complexity of the mixture. The total acquisition time for the experiments ranged between 1-4 h (Borage oil 1272 scans/4 h). Data points 65,536.

Calculations

The GLA carbonyl signals at the 2- and 1,3-positions were well separated from all over carbonyl peaks in the spectra of the triacylglycerols. This allowed the ratio of 2-GLA/1,3-GLA to be determined with reliability and precision in all cases. The method was validated by analysing a test mixture containing 8 triacylglycerols, including trigammalinolenin, of known proportions similar to those present in borage oil. Gross compositions had previously been determined by GLC. Two methods of calculation were employed. The first was a self-contained NMR method calculating the 2-GLA percentage as follows:

Integral of sn-2 Peak for GLA×3×100
Total of all sn-1,2 and 3 integrals

The second used the ratio of 2-GLA/1,3 GLA integrals from the NMR and gross GLA composition as determined by GLC as follows:

Integral of sn-2 Peak for GLA×% GLA from GC analysis×3
Total integrals for GLA at sn-1,2 and 3

Results from both computations were in agreement. We regard the composite NMR-GLC method as more precise since it uses the parameters from each method that can be measured with most accuracy. GLA is a major component of borage oil and therefore the 2-/1,3-GLA ratio can be determined by NMR with precision as the results show. GLC is generally better at determining the composition of even minor fatty acids than NMR but cannot give positional information.

SUMMARY

Details of the experimental data are given in the tables and spectra. It is summarised below. Capsules D and B are sample capsules of provided in the clinical trial reported below.

1. 8-TG-Test-Mixture

| | | | |
|---|---|---|---|
| sn-2 GLA | found | 22.2% | |
| | actual | 22.6% | |
| | error | 1.8% | |

(n) = 2

2. Capsule-D

| | | | |
|---|---|---|---|
| Gross GLA | found | 21.4% (n = 3) | by GLC |
| sn-2 GLA | found | 42.5% (n = 2) | by NMR |
| | error | | +/−1% |

3. Capsule-B

| | | | |
|---|---|---|---|
| Gross GLA | found | 21.1% (n = 3) | by GLC |
| sn-2 GLA | found | 40.8% (n = 2) | by NMR |
| | error | | +/−1% |

In these borage oil samples the GLA content in the sn-2 position is 41-42% i.e. almost double (1.95×) that of the gross composition. A probable typical sample reported in the literature shows an enrichment of 1.8 times gross.

The NMR method can be used to give reliable analytical data for GLA at the sn-2 position. Indeed, it is particularly suited to borage oil because of the non-interference of other fatty acids present. Interestingly results from the NMR method are reported to agree with those from the older derivatisation-chromatographic ones. Our previous estimate (40%) derived from these older methods also agrees with the NMR results.

Treatment Examples

Twenty-eight active relapsing-remitting (two relapses in the preceding 18 months) multiple sclerosis patients (ages ranging from 18 to 65 yrs) were entered into a double-blind placebo controlled trial to investigate the effects of encapsulated borage oil on clinical activity and laboratory parameters over 18 months. This oil was of high Sn-2 γ-linolenic (GLA) content (>40% GLA at Sn-2 ) with low monene (eg. erusic acid) content and had no added Vitamin E, a known immunomodulator.

Patients were recruited from neurology out-patient clinics at two inner city hospitals; hospital informed consent was obtained on first (baseline) visit. Exclusion criteria include any form of steroid or immunosuppressive drug treatment, pregnancy, hyperlipidemia, regular use of aspirin or related drugs and vitamin or fatty acid supplementation within the previous three months.

Only patients meeting all the following criteria were included in the trial: (a) able to provide informed consent prior to treatment, with the full understanding that consent may be withdrawn at any time without prejudice; (b) male or female out-patients aged 18 to 60 years inclusive; (c) have confirmed diagnosis of clinically definite relapsing MS; (d) have had at least three documented clinical relapses in the past two years; (e) have a baseline Expanded Disability Scoring Scale (EDSS) score of 0.0-5.5 inclusive, provided they have well documented exacerbations; and (f) healthy, apart from the MS-related symptoms, as confirmed by the medical history, physical examination and clinical chemistry, urine and haematological tests.

Patients were randomly allocated by the Pharmacy Department to one of three groups each containing 12 patients:
- One clinical group (n=12) to receive placebo (5 g of Polyethylene Glycol 400)
- Second clinical group (n=12) to receive low-dose (5 g) refined *Borage officinalis*
- Third clinical group (n=12) to receive high-dose (15 g) refined *Borage officinalis*

Supplementation was in the form of one gram oil capsules daily (5/day for low dose, 15/day high dose) for 18 months duration. *Borage officinalis* oil and omega-6 polyunsaturated fatty acids are food ingredients that are generally recognised as safe for human consumption (GRAS). There are no classification or labelling requirements under EC regulations.

Clinical assessment included: Extended Disability Scale Scores (EDSS) and clinical relapse record. Venous blood (50 mls) was obtained for laboratory studies on the $1^{st}$, $3^{rd}$, $6^{th}$, $12^{th}$, $15^{th}$, and $18^{th}$ month of supplementation.

The following biochemical and immunological parameters were investigated on each visit for comparison with pre-treatment data and between group data:

Stimulated and unstimulated ex vivo peripheral blood mononuclear cell cytokine production: TGF-β1, IFN-γ, TNF-α, IL-1β, IL-6 and IFN-β, which are implicated in the pathogenesis of MS. Cytokine and related gene expression.

Soluble adhesion molecules in serum particularly ICAM-1 and VCAM-1

Peripheral blood mononuclear cell membrane fatty acids and plasma phospholipid fatty acid composition.

Results are shown in Tables 1 and 2 and FIGS. 1 to 5.

The primary outcome parameter was the number of clinical relapses between baseline (Month 0) and the end of treatment (Month 18). Secondary outcome parameters included: the time to first clinical relapse; severity of relapses, as assessed by EDSS score and the use of steroid treatment; and changes in EDSS at Month 3, 6, 9, 12, and 18 compared to baseline and defined as at least 1.0 point increase in the EDSS that is sustained for 3 months or at least 1.5 point increase on the EDSS from the baseline EDSS that is sustained for 3 months. As this trial did not receive external funding, it was not possible for financial reasons to evaluate MS diseases activity with magnetic resonance imaging. 1 of 3

Eleven patients were in the placebo group, seven patients had been taking low-dose Borage oil, and ten patients had been taking high-dose Borage oil. The study drug was well-tolerated, and there were no serious adverse events during the 18-month trial.

RESULTS

Figure 2:
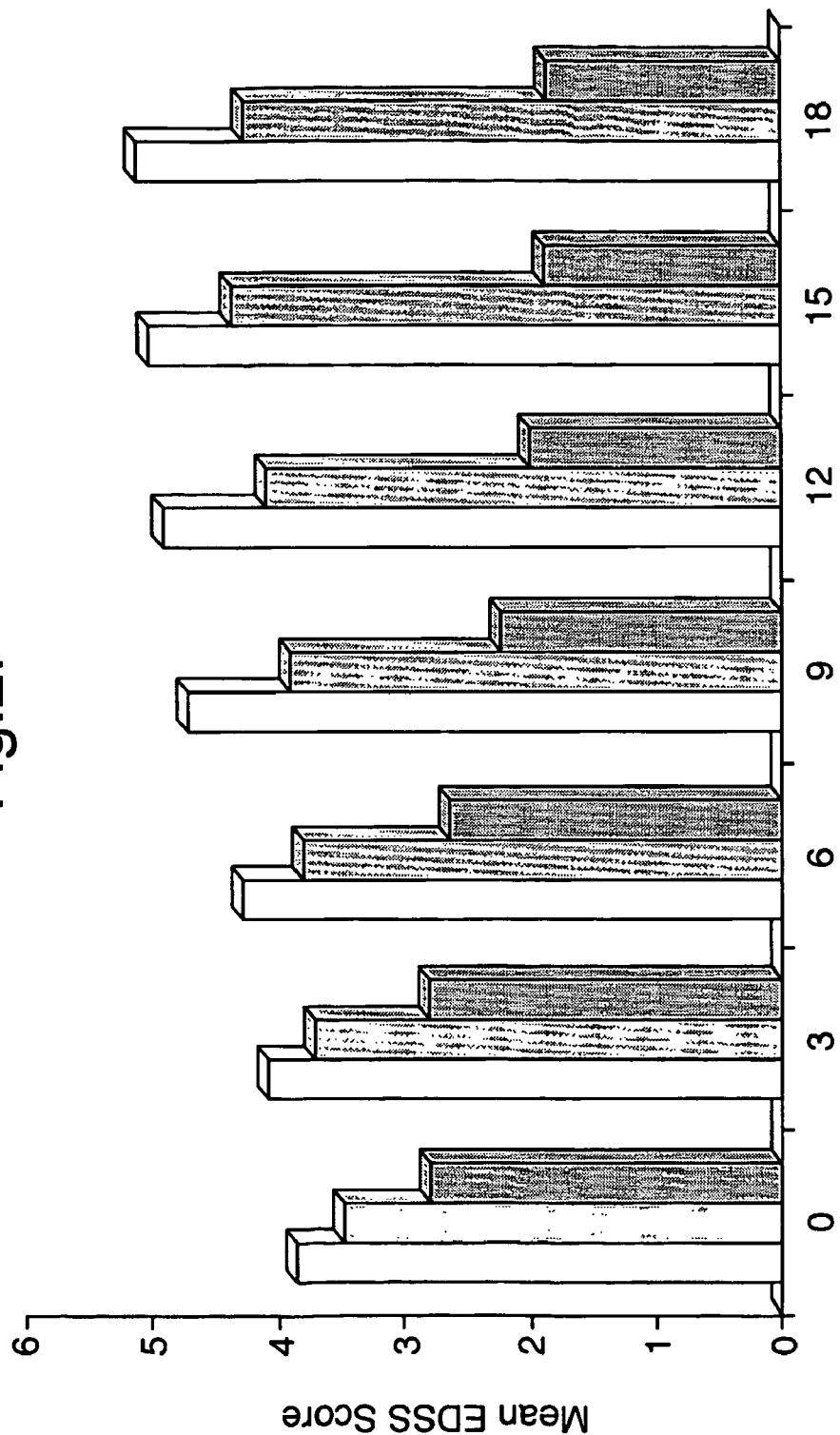
FIG. 2: Shows the effect of placebo and low dose (5 g/day) high sn-2 GLA Borage oil on human MS patient EDSS score as compared to high dose (15 g/day) displayed as a histogram.
Figure 3:
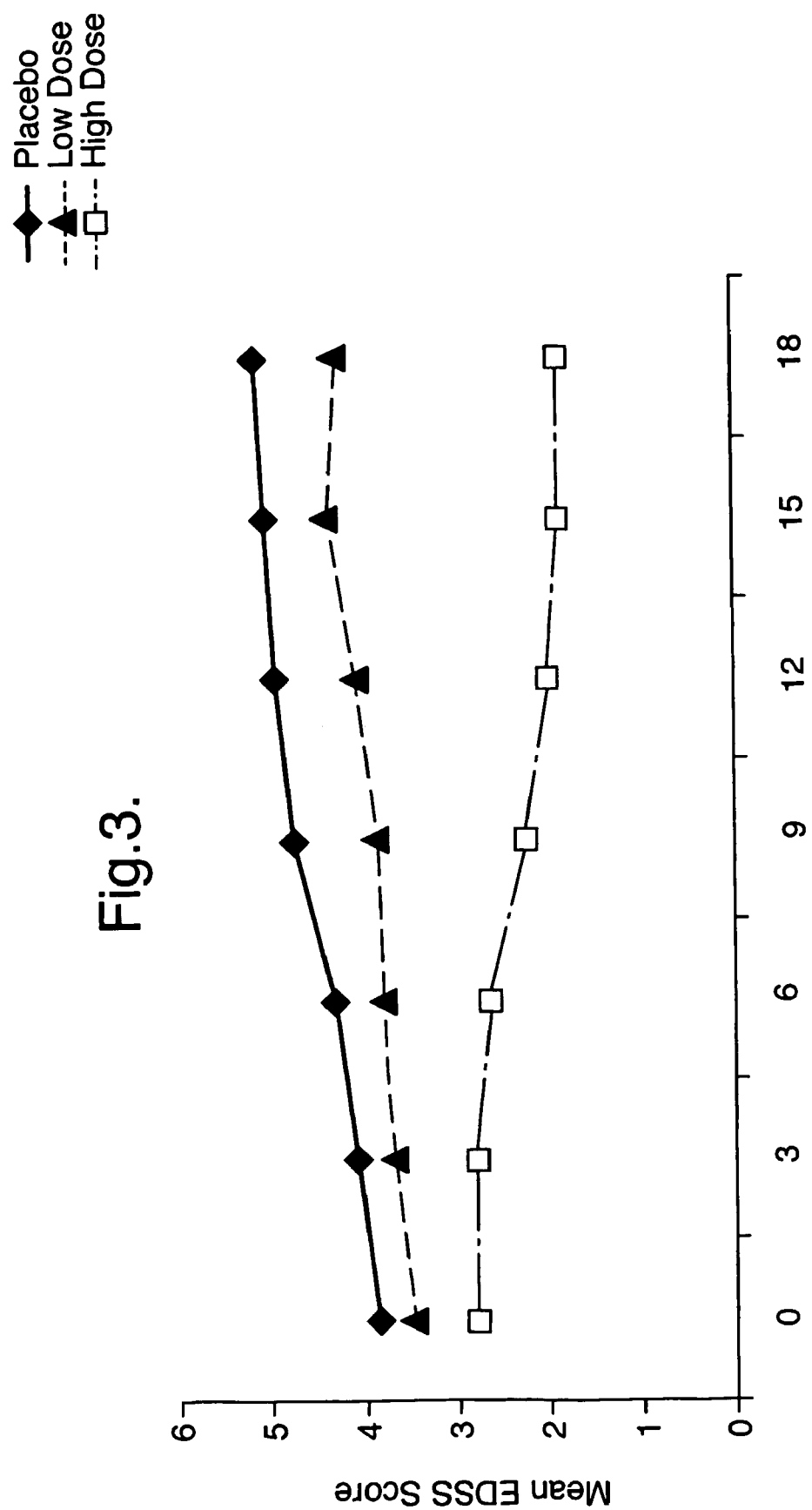
FIG. 3: Shows the effect of placebo, low dose and high dose high sn-2 GLA Borage oil on human MS patient EDSS displayed as a graph.
Figure 4:
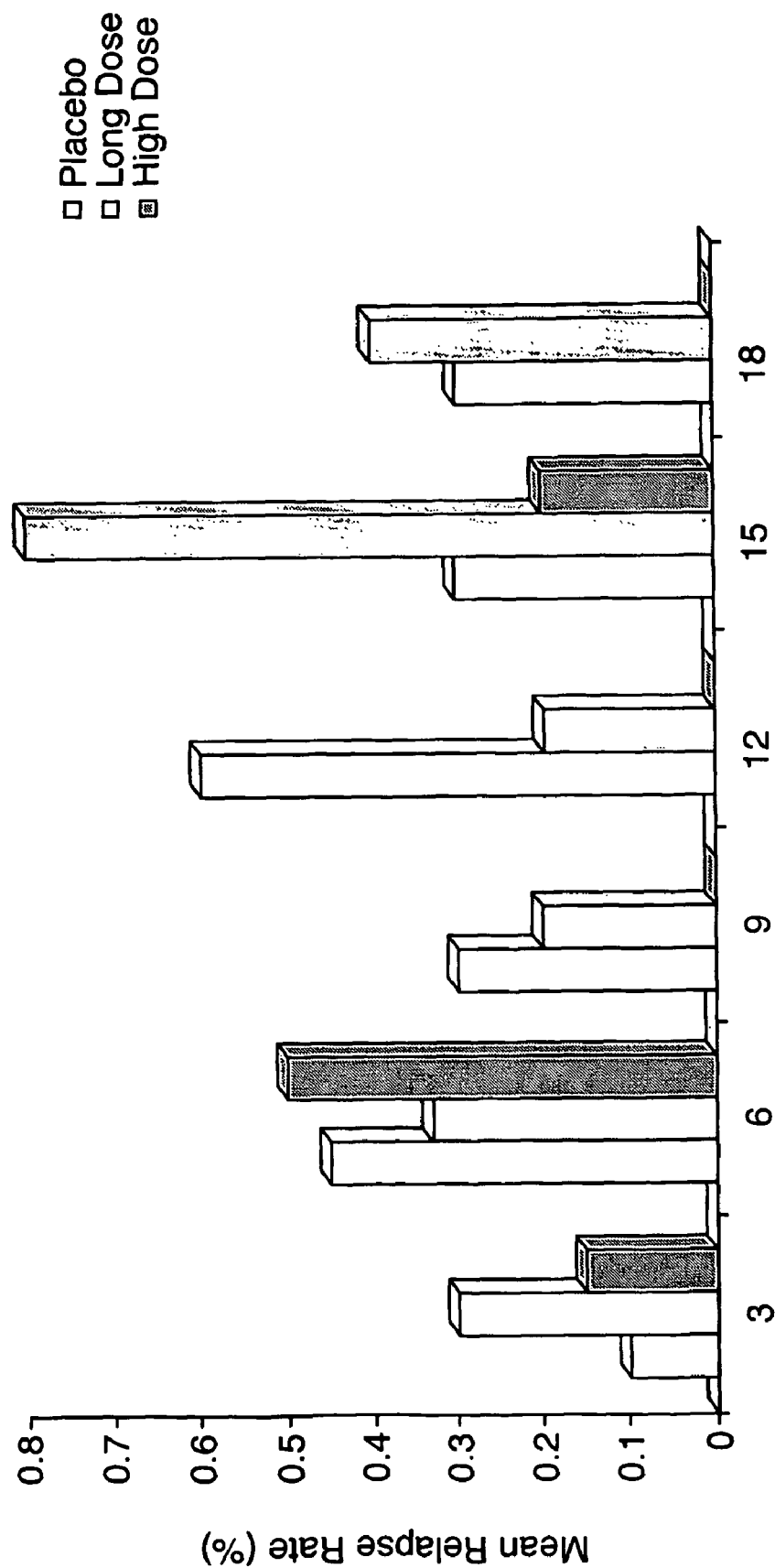
FIG. 4: Shows the effect of placebo, low dose and high dose high sn-2 GLA Borage oil on human MS patient Mean Relapse rate (%) as a histogram
Figure 5:
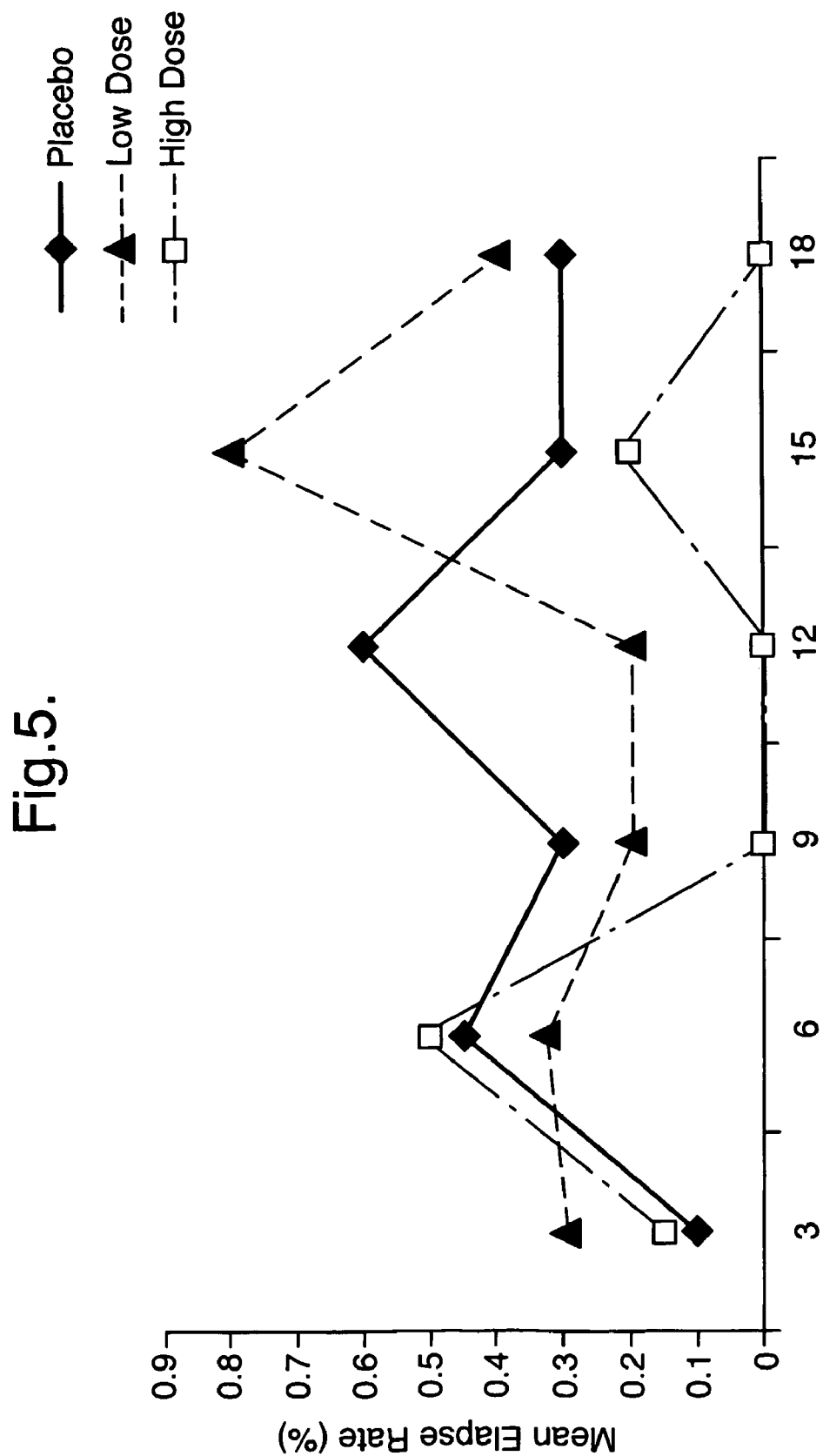
FIG. 5: Shows the effect of placebo, low dose and high dose high sn-2 GLA Borage oil on human MS patient Mean Relapse rate (%) as a graph.

Two patients had developed diarrhoea, both of whom were later confirmed to have been taking high-dose Borage oil. The diarrhoea was mild in one patient, but was moderately severe in the second patient, who later discontinued the study drug. The code was not broken and the diarrhoea had stopped after the discontinuation of the drug, but reappeared upon re-challenge. Therefore, this patient was withdrawn from the trial. The remaining patients who were treated with high-dose Borage oil showed excellent clinical improvement on all primary and secondary outcome criteria. For example, their mean EDSS score after 6 months of treatment had improved from baseline EDSS (FIG. 1). More importantly, the mean number of clinical relapses had significantly reduced after 6 months of treatment when compared to the number of relapses in the placebo group (FIG. 2). In contrast, patients who had been receiving low-dose Borage oil did not show any clinical improvement when compared to the placebo group. In addition to its beneficial effect on MS disease activity, high dose Borage oil provided some symptomatic relief of muscle spasticity (stiffness) and painful sensory symptoms, and also improved cognitive functions.

As can be seen for the figures below, relapse rate after 9, 12 and 18 months was down to zero in the high dose group. The increase seen at 15 months was due to a patient dropping out of this group.

The following are three brief case histories to illustrate the therapeutic benefits of high dose high sn-2 GLA Borage oil. The first two are from the trial while the third is a post trial patient for whom MRI studies were obtained.

Patient 1 (Treatment):

The first patient was a 48 year old woman who had had a clinically active, relapsing remitting MS for 9 years. She had originally worked as a full-time administrator at the local Health Authority, but she was unable to perform her duties because of her severe MS. Therefore, she later worked as a part-time secretary, but still had difficulties in mobilization because of muscles stiffness and sensory disturbances. She was also experiencing severe clinical relapses at an average of one relapse every nine months. Most of these relapses had resulted in hospital admissions for steroid therapy. In view of her active MS, she was recruited into the Borage oil trial. There were no adverse events relating to the study, and after taking the medication for four months, she experienced good improvement in her walking and sensory symptoms.

About nine months after therapy, she was well enough to start full-time employment. In addition, she remained relapse-free for the 18-month duration of the clinical trial. Following the conclusion of the trial, the treatment code revealed that she was taking high-dose Borage oil.

Patient 2 (Control):

The second case was a 46-year old woman who also had a clinically active relapsing remitting MS for 8 years. She had originally worked as a shop assistant, but became unemployed after MS was diagnosed.

Her symptoms included difficulty with mobilisation and painful sensory symptoms in both legs. She had experienced three clinical relapses in the two years preceding the clinical trial, and had been admitted to hospital twice for steroid therapy. Consequently, she was recruited into the Borage oil trial, but her walking continued to deteriorate. Six months into the trial, she need to use a walking stick and also received treatment with Baclofen to reduce low limb spasticity. Approximately ten months after starting the Borage oil trial, she was admitted to hospital because of severe clinical relapse, which was treated with steroids. She later developed bladder disturbances and began to use a wheelchair for long journeys. The treatment code was broken after the conclusion of the 18-month trial, and she was found to have been taking placebo. Since then, she started using a walking frame for journeys exceeding 50 yards.

Patient 3: Treatment (Additional to Trial)

The third case was a 26 year-old man who was diagnosed with definite MS in April 2001. His symptoms had started in 1999 when he complained of diffuse, intractable pain affecting various parts of his body, particularly the left side of the chest and abdomen. This was followed by intermittent numbness in the hands and feet, associated with fluctuating weakness. There were also distressing bladder symptoms in the form of urinary frequency and urgency. The diagnosis of MS in 2001 was based on his relapsing remitting symptoms, and was confirmed by positive cerebrospinal fluid analysis and magnetic resonance imaging (MRI) of the brain, which showed multiple white matter abnormalities in both cerebral hemispheres. Symptoms did not respond to various pharmaceutical therapies.

In April 2003, oral supplementation with the present high dose Borage oil was commenced. The patient reported dramatic improvement in his symptoms within three months of starting this oral supplementation. His painful sensory symptoms disappeared completely. He reported no numbness or weakness since May 2003, and noticed significant improvement in his bladder control. The oral supplementation caused no adverse events. A repeat brain MRI was undertaken to verify the reported improvement in Mr N's symptoms. The repeat MRI showed a reduction in the size and distribution of the white matter abnormalities.

TABLE 1

Compositional (% Total FAs) Characteristics of Various Oils and their Protective Effects in EAE

| Treatment | 18:2n-6 | 18:3n-6 | 18:2n-6/18:3n-6 | 18:1n-9 | INCIDENCE OF EAE |
|---|---|---|---|---|---|
| FGO | 17 | 20 | 0.6 | 35 | 0/10 |
| BOO | 37 | 24 | 1.5 | 15 | 3/10 |
| EPO | 71 | 9.4 | 7.5 | 9 | 7/10 |
| SAF | 66 | — | — | 17 | 9/10 |
| Controls | — | — | — | — | 9/10 |

FGO, Fungal Oil;
BOO, Borage Oil;
EPO, Evening Primrose Oil,
SAF, Safflower Oil.

TABLE 2

Treatment Groups-Borage oil-MS trial

| | | Female | Male | Mean Relapse Rate (in past two years) | Mean Base EDSS | Number |
|---|---|---|---|---|---|---|
| Group | Placebo | 7 | 4 | 2.6 | 3.9 | 11 |
| | Low Dose | 5 | 2 | 2.9 | 3.5 | 7 |
| | High Dose | 8 | 2 | 3.4 | 2.8 | 10 |
| Total | | 20 | 8 | 2.9 | 3.4 | 28 |

TABLE 3

Molecular Species Comparison of Triacylglycerol-GLA (TG-GLA), Ethyl-Ester-GLA (EE-GLA) and *Borago Officinalis* Oil-GLA (BOR-GLA) in MOG-induced CREAE in SJL Mice

| Treatment | No. with EAE | Mean Clinical Score |
|---|---|---|
| Control | 10/11 | 3.3 ± 1.3 |
| EE-GLA[a] | 5/6 | 3.0 ± 0.8 |
| TG-GLA[a] | 3/6 | 1.0 ± 1.3[c] |
| BOR-GLA[b] | 3/6 | 1.0 ± 1.2[c] |

[a]Animals given 100 μl of test lipid;
[b]250 μl BOR-GLA given. Significance of difference compared with controls,
[c]$p < 0.05$

TABLE 4

Effect of enriched black-currant seed oil (73% GLA) on the incidence of EAE

| | % Incidence of EAE (Days after immunisation) | | |
|---|---|---|---|
| | 13 | 17 | 21 |
| Controls (n = 10) | 60 | 90 | 10 |
| Blackcurrant (n = 10) | 10 | 80 | 70 |

Note:
Blackcurrant oil delays the incidence but does not provide full protection. Animals were fed 7 days after sensitization (immunisation).

TABLE 5

ANALYSIS REPORTS ON TRIAL BORAGE OIL
(% Total Fatty Acids)

| Fatty Acids % | SAMPLE 1 | SAMPLE 2 | SAMPLE 3 | SAMPLE 4 |
|---|---|---|---|---|
| 16:0 | 13.29 | 13.47 | 12.86 | 13.11 |
| 16:1n7 | 0.21 | 0.22 | 0.21 | 0.21 |
| 18:0 | 3.50 | 3.47 | 3.54 | 3.50 |
| 18:1n9 | 16.22 | 16.22 | 16.33 | 16.22 |
| 18:1n7 | 0.64 | 0.66 | 0.65 | 0.64 |
| 18:2n6 | 38.00 | 38.01 | 38.25 | 37.96 |
| 18:3n6 | 22.59 | 22.66 | 22.69 | 22.56 |
| 18:3n3 | 0.18 | 0.18 | 0.17 | 0.19 |
| 20:0 | 0.20 | 0.18 | 0.20 | 0.21 |
| 20:1n9 | 2.96 | 2.88 | 3.06 | 3.06 |
| 22:1n9 | 1.55 | 1.41 | 1.50 | 1.58 |
| 24:1n9 | 0.60 | 0.63 | 0.52 | 0.71 |

TABLE 6

ANALYSIS OF A NON-TRIAL BORAGE OIL
(% Total Fatty Acids)

| Fatty Acids | % Total Fatty Acids |
|---|---|
| 16:0 | 11.07 |
| 16:1n-7 | 0.17 |
| 18:0 | 3.70 |
| 18:1n-9 | 16.37 |
| 18:1n-7 | 0.66 |
| 18:2n-6 | 37.71 |
| 18:3n-6 | 21.89 |
| 18:3n-3 | 0.17 |
| 20:0 | 0.25 |
| 20:1n-9 | 3.79 ↑ |
| 22:1n-9 | 2.38 ↑ (high) |
| 24:1n-9 | 1.47 ↑ |

The invention claimed is:

1. A method of treating a patient in need of therapy for a neurodegenerative disease comprising administering to that patient a therapeutically effective dose of a triglyceride oil containing both γ-linolenic acid and linoleic acid residues as triglyceride ester, the ratio of γ-linolenic acid to linoleic acid residues at the sn-2 position of the triglyceride being at least 0.8; the amount of γ-linolenic acid residues at the sn-2 position being at least 18%, wherein the oil is administered at a dose sufficient to maintain or elevate TGF-β1 levels in the patient at a therapeutic level.

2. A method as claimed in claim 1 wherein the therapeutic level is such as to produce a TGF-β1/TNF-α ratio of at least 0.5 in blood of a patient, after 18 months of daily dosing.

3. A method as claimed in claim 2 wherein the ratio is at least 0.75.

4. A method as claimed in claim 2 wherein the ratio is at least 1.

5. A method as claimed in claim 1 wherein the amount of oil administered is between 3 and 30 grams per day.

6. A method as claimed in claim 1 wherein the oil is administered orally.

7. A method as claimed in claim 1 wherein the dose is sufficient to administer at least 1 gram of γ-linolenic acid residues, as residues in the sn-2 position, excluding other γ-linolenic acid content of the oil.

8. A method as claimed in claim 1 wherein the amount of γ-linolenic acid in the sn-2 position in the dose of oil is sufficient to administer at least 2 grams of said sn-2 γ-linolenic acid.

9. A method as claimed in claim 1 wherein the dose is between 8 and 20 grams.

10. A method as claimed in claim 1 wherein in addition to the γ-linolenic acid and linoleic acid fatty acid residues, the triglyceride includes an esterified fatty acid that is non-structural.

11. A method as claimed in claim 10 wherein the triglyceride contains oleic acid residues.

12. A method as claimed in claim 1 wherein the oil is that obtained from a fungus or a plant selected from the group consisting of *Mucor* and *Borago* species.

13. A method as claimed in claim 12 wherein the fungus or plant is selected from *Mucor javanicus* and *Borago officianalis*.

14. A method as claimed in claim 1 wherein the oil is a *Borago* oil in which the percentage of esterified γ-linolenic acid at the sn-2 position is at least 35% of fatty acid residues at that position.

15. A method as claimed in claim 14 wherein the percentage of esterified γ-linolenic acid at the sn-2 position is at least 39% of fatty acid residues at that position.

16. A method as claimed in claim 14 wherein the percentage of esterified γ-linolenic acid at the sn-2 position is at least 45% of fatty acid residues at that position.

17. A method as claimed in claim 1 wherein the fatty acid residues in the sn-1 and sn-3 position include linoleic, oleic and γ-linolenic acid residues.

18. A method as claimed in claim 1 wherein the triglyceride oil has an oleic acid content in one or both of the sn-1 and sn-3 positions of in excess of 12%.

19. A method as claimed in claim 1 wherein the oil is *Mucor* oil and; the total percentage of esterified γ-linolenic acid residues at the sn-2 position is at least 20% of fatty acid residues at that position.

20. A method as claimed in claim 19 wherein the triglyceride oil has in excess of 45% of the sn-2 fatty acid residues as oleic acid residues.

21. A method as claimed in claim 19 wherein the triglyceride oil has in excess of 50% of the sn-2 fatty acids as oleic acid residues.

22. A method as claimed in claim 1 wherein the triglyceride oil contains less than 5% monoenoic fatty acid residues as % total fatty acid residues.

23. A method as claimed in claim 22 wherein the triglyceride oil contains less than 5% in total erucic acid (22:1n-9), 24:1n-9 (nervonic acid) and 20:1n-9 (gadoleic acid) as a percentage of total fatty acid residues.

24. A method as claimed in claim 22 wherein the amount of said acid is between 1% and 5% of fatty acid residues in the oil.

25. A method as claimed in claim 1 wherein the oil has no added vitamin E.

26. A method as claimed in claim 1 wherein vitamin E is added in an amount between 0 and 0.1 mg/g.

27. A method as claimed in claim 1 wherein the neurodegenerative disease is arrested or neuronal function is restored.

28. A method as claimed in claim 1 wherein treatment is for multiple sclerosis or the degenerative sequelae associated with head trauma, stroke and intracranial bleeds.

29. A method as claimed in claim 28 wherein the treatment repairs lesions.

30. A method as claimed in claim 1 wherein the treatment uses a dose sufficient to relieve muscle spasticity and/or pain.

31. A method as claimed in claim 1 wherein the dosage is sufficient to improve cognitive function.

32. A method as claimed in claim 1 wherein the dosage is sufficient to eliminate relapses.

33. A method as claimed in claim 1 wherein the dosage is sufficient to improve the patients EDSS score by at least 1 unit over a period of 1 year's treatment.

34. A method as claimed in claim 1 wherein the dosage is sufficient to restore EDSS of a patient with EDSS above 2.5 to below 2 over a period of 1 year's treatment.

* * * * *